United States Patent [19]

Haveson

[11] Patent Number: 5,798,101
[45] Date of Patent: Aug. 25, 1998

[54] HERBAL APPETITE SUPPRESSANT AND WEIGHT LOSS COMPOSITION

[75] Inventor: Brian Haveson, Yardley, Pa.

[73] Assignee: HPF, L.L.C., Horsham, Pa.

[21] Appl. No.: 847,542

[22] Filed: May 1, 1997

Related U.S. Application Data

[60] Provisional application No. 60/036,339, Jan. 22, 1997 and provisional application No. 60/038,128, Mar. 3, 1997.

[51] Int. Cl.$^6$ .......................... A61K 35/78; A61K 31/135
[52] U.S. Cl. .......................... 424/195.1; 514/653
[58] Field of Search .................. 424/195.1; 514/653

[56] References Cited

U.S. PATENT DOCUMENTS

| | | | |
|---|---|---|---|
| 5,019,594 | 5/1991 | Wurtman et al. | 514/561 |
| 5,055,460 | 10/1991 | Friedlander | 514/161 |
| 5,273,754 | 12/1993 | Mann | 424/440 |
| 5,422,352 | 6/1995 | Astrup | 514/264 |
| 5,436,230 | 7/1995 | Soudant et al. | 514/21 |
| 5,543,405 | 8/1996 | Keown et al. | 514/188 |

OTHER PUBLICATIONS

Shepherd, D., Battling The Winter Blues, 1997, pp. 20–22.
Pasquali, R., Effects of Chronic ... In Obese Subjects, 1992, pp. 85–92.
Astrup, A., Pharmacological and Clinical Studies ...., Nov. 4, 1996, pp. 537S–540S.
Pasquali, R., Does Ephedrine Promote ... Obese Women ...., Oct. 28, 1986, pp. 163–168.

*Primary Examiner*—Raymond Henley, III
*Attorney, Agent, or Firm*—Louis Weinstein

[57] ABSTRACT

The present invention is directed to herbal compositions which reduce weight, maintain weight loss over an extended period of time, and act as an appetite suppressant. The composition consists of St. John's Wort with or without caffeine or other appetite suppressants known in the art, and also a composition comprising St. John's Wart (hypericin) and Mahuang (*Ephedra sinica* or ephedrine). Another composition disclosed comprises a combination of the above herbs with caffeine.

11 Claims, No Drawings

HERBAL APPETITE SUPPRESSANT AND WEIGHT LOSS COMPOSITION

This application claims the benefit under 35 USC 119(e) of provisonal application Ser. Nos.60/036,339, filed Jan. 22, 1997 and 60/038,128 filed Mar. 3, 1997.

FIELD OF THE INVENTION

The invention relates to compositions for reducing weight in humans and/or animals and more particularly to herbal compositions for achieving the desired result.

BACKGROUND OF THE INVENTION

This invention relates to herbal compositions for reducing weight, maintaining weight loss over an extended period of time and suppressing appetite in a human or a domestic animal.

Examples of known appetite reducing agents are ephedrine which is an extract of the herb Mahuang (*Ephedra sinica*), phenylpropanolamine (PPA), amphetamines and fenfluramine alone or in combination with caffeine. Caffeine functions probably to reduce fatigue as caffeine has stimulating properties. Phenylpropanolamine (PPA) is a popular over-the-counter drug for appetite suppression and its side effects are well documented.

Several herbal compositions have been developed for reducing weight in humans or domestic animals. U.S. Pat. No. 5,422,352 discloses a composition of ephedrine and caffeine in a ratio of about 1:12. U.S. Pat. No. 5,019,594 discloses a method for decreasing appetite by administering a composition containing ephedrine or other indirect acting sympathomimetic drugs and tyrosine. U.S. Pat. No. 5,273,754 discloses an appetite suppressant composition comprising a heating and a cooling carminative substance, which composition may also include an amino acid and an anxiolytic substance. One of the anxiolytic substances disclosed is St. Joh's Wort. U.S. Pat. No. 5,543,405 discloses a weight reduction composition comprising a sympathomimetic agent and a mineral cation salt or chelate. Preferred is a composition comprising ephedrine and chromium picolinate. U.S. Pat. No. 5,055,460 discloses a composition for reducing weight comprising ephedrine, acetylsalicylic acid and caffeine.

However, none of the methods for weight reduction or appetite suppression disclose a composition consisting of St. John's Wort (hypericin), or a composition comprising St. John's Wort and Mahuang (*Ephedra sinica* or ephedrine) which are disclosed in the present invention. The synergistic effect of St. John's Wort and Mahuang have been shown to be unexpectedly superior than the effect of the individual components.

SUMMARY OF THE INVENTION

The present invention discloses herbal compositions effective in reducing weight, maintaining weight loss and suppressing appetite comprising comprising St. John's Wort (hypericin) and Mahuang (*Ephedra sinica* or ephedrine). When taken in combination, St. John's Wort and Mahuang act synergistically to increase serotonin levels in the brain to effect appetite suppression and caloric expenditure increase in the body. These weight reduction and appetite suppressant compositions are presented in a variety of formulations, with or without other weight reduction active ingredients such as phenalpropanolamine and caffeine.

BRIEF DESCRIPTION OF THE INVENTION

It is a well established fact that overweight and obesity is an unhealthy condition. It is therefore logical that substances aiding or resulting in weight reduction would be beneficial to a society where millions suffer from obesity, as long as the substance is safe and effective when taken as directed. This condition may be related to a genetic trait and/or to environmental factors. See, generally, Ravussin, Lillioja, Knowler, Reduced Rate Of Energy Expenditure As A Risk factor For Body Weight Gain, New Jr. Eng. of Med., 318, p. 467, 1988.

Over-weight and obesity are chronic conditions which are highly prevalent in industrialized society. These conditions are associated not only with social stigma but are also associated with decreased longevity and numerous medical problems such as diabetes, reproductive disorders, dermatological disorders, varicose veins, arthritis, heart disease, cancer, etc.

Over-weight and obesity is a condition characterized by the excessive accumulation of fat in the body as a consequence of an energy intake which is greater than energy expenditure. Over-weight is present if the body weight exceeds a "desirable weight", whereas obesity represents a condition where the weight is 20% or more above the desirable weight. Desirable weight for humans is defined in the Metropolitan Height And Weight tables as the midpoint of the range of medium frame individuals. See, JAMA,260, 2547–48, 1988.

Existing therapies for over-weight and obesity basically include a treatment to establish a negative energy balance. This may be accomplished by reduction of energy intake, for example, a low calorie diet; or an increase in energy expenditure, for example, by increased physical exercise; or by ingestion of a sympathomimetic drug which stimulates thermogenesis, i.e., increases the metabolic rate of the body in humans and animals. Known thermogenic drugs are ephedrine, phenylpropanolamine and caffeine. See, for example, Astrup, A.V., Treatment Of Obesity With Thermogenic Agents, Nutrition, 5, p. 70, 1989; Bray, Nutrition Reviews, 49, p. 33, 1991.

While energy expenditures may increase 10-fold during exercise, the thermogenic effect of pharmacological agents is much more modest. Sympathomimetic compounds and beta adregenic agonists can increase resting energy expenditure by 10% to 15% and slightly potentiate the effect of foods. Energy expenditure may be increased 5% to 10% on a 24-hour basis. See, generally, Astrup, Breum, Tourbo, Pharmacological And Clinical Studies Of Ephedrine And Other Thermogenic Agonists, Obesity Research, 3, p. 537, 1995.

Drugs which are used for reducing weight or obesity suppress appetite by acting the on noradrenergic neurotransmitter such as mazindol and derivatives of phenethylamine, for example, phenylpropanolamine, phentermine, amphetamine, methamphetamine. Also well known in the art are the use of drugs which act on the serotonin neurotransmitter such as fenfluramine, tryptophan, fluoxetine and sertraline. However, all these drugs have side effects.

There is, therefore, a need for a drug which will reduce the weight of overweight or obese persons without side-effects and which will also help obese and overweight subjects maintain the reduced weight level.

OBJECTS OF THE INVENTION

It is therefore an object of the present invention to provide a regimen that is useful in returning the body weight of overweight or obese subjects to a lower and preferably normal body weight.

It is another object of the present invention to provide a therapy for overweight or obesity that results in maintenance of the lowered body weight over an extended period of time.

DETAILED DESCRIPTION OF THE INVENTION AND PREFERRED EMBODIMENTS THEREOF

The present invention is directed to a composition of St. John's Wort, and also to a composition comprising St. John's Wort (hypericin) and Mahuang (*Ephedra sinica*, or its extract ephedrine).

St. John's Wort is a herb of the hypericaceae family which contains the therapeutically active ingredient hypericin. St. John's Wort has antidepressant properties for which it is widely used in Europe. Numerous publications and meta-analysis strongly suggests the antidepressant efficacy through seratonergic mechanisms. However, it was unexpectedly found that St. John's Wort also functions to reduce weight and also acts as an appetite suppressant, most likely by controlling serotonin levels. See BMJ 1996; 313:253-8 St. John's Wort for Depression—An Overview and Meta-analysis Of Randomized clinical Trials; K. Linde, et al.

The dosage form of St. John's medication contains its extract at a concentration of 0.3% Hypercum perforatum. For efficacy in providing weight reduction, St. John's Wort should be present in an amount ranging from 10 mg to 2500 mg per dose per day, preferably 100 mg to 800 mg per dose per day or 500 mg per dose per day. Most preferably, St John's Wort is present in amount of 400 mg per dose which is to be taken two times per day. Other weight reduction compositions such as caffeine may be taken with St. John's Wort.

Another composition which is effective in reducing weight and suppressing appetite is a composition comprising St. John's Wort (hypericin) and Mahuang (*Ephedra sinica* or ephedrine) Mahuang is also a naturally occurring herb which aids in weight reduction through its active ingredient the sympathomimetic compound *Ephedra sinica* or its extract ephedrine. When used in combination with St. John's Wort, Mahuang should be present in an amount ranging from 5 mg to 1500 mg per dose per day, and most preferably at a concentration of two doses of 250 mg each per day.

Both St. John's Wort and Mahuang are safe and effective when used as directed and side effects are minor or none. High doses of Mahuang are associated with sympathomimetic simulation and attendant side effects. Accordingly, low doses are recommended in the medication and subjects who have high blood pressure or cardiac arrhythmias are not good candidates for this drug regimen.

If both St. John's Wort and Mahuang are taken, it is recommended that Mahuang be taken separately in the morning and St. John's Wort in the afternoon before dinner.

Good results were observed in a clinical study according to the present invention by using a pharmaceutical tablet composition consisting of a composition comprising St. John's Wort and Mahuang in overweight or obese subjects. However, the results of the clinical studies detailed below clearly demonstrate that the action exerted by the combination of St. John's Wort and Mahuang is due to an unexpected synergistic effect of the two drugs.

The herbal components (St. John's Wort and Mahuang) may be used for weight reduction and appetite suppressant without being further processed, or they may be used as extracts thereof. For example, St. John's Wort herb may be dried, powdered and used in the powdered form as the active ingredient in a oral dosage form such as a pill or a capsule. Alternatively, hypericin, the active ingredient of St. John's Wort may be extracted from the herb by soaking the crushed herb in an alcohol/water solution and the extracted active ingredient dried by spray drying or evaporation.

The composition according to the present invention may be formulated for administration by any conventional route such as oral, rectal, nasal, topical (dermal) or parenteral. Thus the composition may be in the form of tablets, capsules, suspensions, emulsions, solutions, suppositories, sprays or injectibles. Formulations for oral use include tablets which contain the active ingredient in admixture with pharmaceutically acceptable inert excipients. These excipients may be, for example, inert diluents such as calcium carbonate, sodium chloride, lactose, calcium phosphate, sodium phosphate, etc.; granulating and disintegrating agents, for example, potato starch, alginic acid, etc.; binding agents, for example, starch, gelatin or acacia, etc.; and lubricating agents for example, magnesium stearate, stearic acid or talc. Other pharmaceutically acceptable excipients can be colorants, flavoring agents, plasticizers, humectants, etc. The tablets may be uncoated or they may be coated by known techniques.

Alternatively, the active ingredients of the weight reduction formulation may be delivered over an extended time period by delaying disintegration and absorption in the gastrointestinal tract to provide a sustained release effect. For example, a time delay material such as glyceral monostearate or glycerol distearate may be employed. The active ingredient may be placed in an extended release dosage form by techniques which are well known in the art. See, for example, Baker, Richard, Controlled Release Of Biologically Active Agents, John Wiley And Sons, 1986. The inactive excipients in a tablet may include calcium carbonate, dicalcium phosphate, microcrytalline cellulose, croscarmellose sodium, stearic acid, silica, magnesium stearate and pharmaceutical glaze. Alternatively, the active ingredient or extract thereof may be delivered in a soft or hard gel capsule by mixing the active ingredient with water or an oil medium such as peanut oil, liquid paraffin, or olive oil and enclosing it within the capsule or gel capsule.

The dosage may also be administered as an oral liquid dosage form by suspending the active ingredients or extracts thereof in an aqueous solution in admixture with a dispersing or wetting agent, suspending agent and one or more preservatives. Suitable dispersing or wetting agents are, for example, naturally occurring phosphatides, for example, lecithin, or condensation products of ethylene oxide, fatty acids, long chain aliphatic acids, or a partial ester derived from fatty acids and a hexitol or hexitol anhydrides, for example, polyoxyethylene stearate, polyoxyethylene sorbitol monooleate, polyoxyethylene sorbitan monooleate, etc. Suitable suspending agents are, for example, sodium carboxymethylcellulose, methylcellulose, sodium alginate, etc.

The pharmaceutical formulation may also be delivered parenterally in dosage forms containing conventional pharmaceutically acceptable carriers and adjuvants. The formulation and preparation of such compositions is well known to those skilled in the art. For example, specific formulations can be found in the text Remington's Pharmaceutical Sciences, Mack Publishing Co., Easton, Pa., 1995. The active ingredients may be dissolved in vehicles such as water, isotonic sodium hydroxide solutions, etc. The aqueous formulations may also contain a preservative such as methyl, ethyl or n-propyl p-hydroxybenzoate.

For rectal applications, suitable dosage forms for a composition according to the present invention include suppositories (emulsion or suspension type), and rectal gelatin capsules (solution or suspensions). In a typical suppository formulation, the active ingredients of the two herbs are combined with an appropriate pharmaceutically acceptable suppository base such as cocoa butter, esterified acids, glycerinated gelatin, and various water soluble or dispersable bases like polyethylene glycols and polyoxyethylene glycols and polyoxyethylene sorbitan fatty acid esters.

To prepare the weight loss and appetite suppressant of the present invention in a tablet form, the extract of the two herbs were combined with excipients in an appropriate ratio and thereafter tableted by methods which are well known in the art. See, for example, Remington's Pharmaceutical Sciences, Mack Publishing Co., Easton, Pa., 1995.

EXAMPLE 1

Overweight and obese patients were placed on a low calorie diet and a daily dosage of St. John's Wort effective to control appetite and reduce weight and maintain the weight loss is 10 mg to 2100 mg per day, with and without caffeine. It was found that over a two month period, over 90% of the subjects lost an average of 4 pounds per month, were able to maintain the weight loss, and reported a decreased craving for food and a decreased appetite.

EXAMPLE 2

A dose response open-label study of the thermogenic effect of St. John Wort in combination with Mahuang was conducted. The concentration range over which Mahaung is effective to control appetite, reduce weight and maintain the weight loss is from 10 mg to 2500 mg per day.

The aim of the study was to assess the effectiveness, tolerability and safety of oral administration of St. John's Wort at a dosage of 400 mg twice daily and a Mahuang dosage of 250 mg twice daily over a 6 week period for the treatment of overweight and appetite suppression. Changes in weight and body composition measurements were primary effectiveness variables. The aim of the study was to determine if fat is preferentially lost when the two herbs are combined with the diet. Appetite suppression was a secondary effectiveness variable.

The study was conducted in subjects with a body mass index of 27 to 32 kg/square meter. Fifteen overweight but otherwise healthy subjects were selected at random for the study. The subjects were supplied with two weeks supply of 28 caplets and one of three calorie diet plans. The subjects were directed to swallow a caplet comprising one 200 mg St. John's Wort and 125 mg of Mahuang 30 to 60 minutes before breakfast and to repeat the same dosage before dinner with a glass of water.

Specifically excluded from this study were subjects who required or were currently taking any significant medication other than analgesics on an occasional basis such as drugs containing sympathomimetics amines, MAO inhibitors and other drugs indicated for weight reduction.

The subjects were instructed to visit the clinic every week to weigh-in and pick up the necessary combined St. John's Wort and Mahuang tablets. On each visit the subjects were also monitored for blood pressure, temperature, body fat by bioimpendence analysis and anthropometry, and circumference measurements of the chest, waist and hips.

At the end of the six weeks study, the 12 subjects lost an average of 8 pounds. The subjects also reported on the effects of the herbal therapy as it related to appetite control, feeling of fullness and snack cravings. 87% of the subjects reported a suppression of appetite; 81% reported satisfaction with less food during a meal, and 81% reported that they were less inclined to snack between meals.

It will be apparent to one of ordinary skill in the art that many changes and modifications can be made to the present disclosure without departing from the spirit and scope of the invention as set forth herein.

A latitude of modification, change and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein described.

What is claimed is:

1. A composition comprising a dosage of a member selected from the group consisting of St. John's Wort and hypericin and a member selected from the group consisting of Mahuang extract, *Ephedra sinica* and ephedrine in an amount effective for reducing weight and maintaining the weight loss.

2. A composition comprising a dosage of a member selected from the group consisting of St. John's Wort and hypericin and a member selected from the group consisting of Mahuang extract *Ephedra sinica* and ephedrine in an amount effective for suppressing appetite.

3. The composition of claim 1 wherein St. John's Wort is present in an amount ranging from 10 mg to 2500 mg.

4. The composition of claim 1 wherein the amount of St. John's Wort is 400 mg.

5. The composition of claim 1 wherein the amount of St. John's Wort ranges from 10 mg to 2500 mg, and the dosage of Mahuang ranges from 5 mg to 1500 mg.

6. The composition of claim 1 wherein St. John's Wort is present in an amount of 500 mg per day and Mahuang is present in an amount of 800 mg per dose.

7. The composition of claim 1 in sustained release form.

8. The composition of claim 1 in unit dosage form.

9. The composition of claim 1, further comprising an agent selected from the group consisting of electrolytes, buffers, colorants, aromatic agents, flavoring agents, emulsifying agents, compounding agents, formulation agents, permeation enhancers and other weight reduction agents and bulking agents.

10. A method for obtaining weight reduction in humans and animals including taking a daily dosage of St. John's Wort in the range of 10 mg to 2100 mg per day and a daily dosage of a member selected from the group consisting of Mahuang extract, *Ephedra sinica* and ephedrine in the range of 10 mg to 2500 mg.

11. A method for obtaining and maintaining weight reduction in humans and animals including taking a composition comprising a daily dosage of St. John's Wort in the range of 10 mg to 2100 mg per day and a daily dosage of a member selected from the group consisting of Mahuang extract, *Ephedra sinica* and ephedrine in the range of 10 mg to 2500 mg and administering to the subject, after a predetermined weight is attained, a weight maintaining effective amount of the composition.

* * * * *

UNITED STATES PATENT AND TRADEMARK OFFICE
CERTIFICATE OF CORRECTION

PATENT NO. : 5,798,101
DATED : August 25, 1998
INVENTOR(S) : Haveson

It is certified that error appears in the above-identified patent and that said Letters Patent is hereby corrected as shown below:

Col. 2, line 48, after "acting" delete --the--.

Col. 2, line 48, after "on" insert --the--.

Col. 3, delete lines 20-29 in their entirety.

Col. 6, line 21, Claim 1, delete "hypercin".

Col. 6, line 22, Claim 1, delete "Ephedra sinica".

Col. 6, line 27, Claim 2, delete "hypercin"

Col. 6, line 28, Claim 2, delete "Ephredra sinica".

Signed and Sealed this

Thirteenth Day of July, 1999

Attest:

Q. TODD DICKINSON

Attesting Officer

Acting Commissioner of Patents and Trademarks